(12) United States Patent
Whitman et al.

(10) Patent No.: US 8,814,785 B2
(45) Date of Patent: Aug. 26, 2014

(54) ORIFICE INTRODUCER DEVICE

(75) Inventors: Michael P. Whitman, New Hope, PA (US); Gerald Dorros, Scottsdale, AZ (US); Jeremy Hill, Middlebury, CT (US)

(73) Assignee: Covidien LP, Mansfield, MA (US)

( * ) Notice: Subject to any disclaimer, the term of this patent is extended or adjusted under 35 U.S.C. 154(b) by 161 days.

(21) Appl. No.: 12/966,234

(22) Filed: Dec. 13, 2010

(65) Prior Publication Data

US 2011/0082342 A1      Apr. 7, 2011

Related U.S. Application Data

(62) Division of application No. 10/632,271, filed on Jul. 31, 2003, now Pat. No. 7,874,981.

(60) Provisional application No. 60/400,023, filed on Jul. 31, 2002.

(51) Int. Cl.
*A61B 1/00* (2006.01)

(52) U.S. Cl.
USPC ........................................ 600/184; 606/108

(58) Field of Classification Search
USPC ......... 600/114, 115, 127, 129, 184, 201, 206; 604/163, 164.01, 164.03, 164.05, 604/164.08, 164.1, 164.11; 606/161, 191, 606/108

See application file for complete search history.

(56) References Cited

U.S. PATENT DOCUMENTS

| | | | |
|---|---|---|---|
| 668,879 A * | 2/1901 | Miller ............................ | 27/21.1 |
| 3,256,875 A | 6/1966 | Tsepelev | |
| 3,877,429 A * | 4/1975 | Rasumoff ..................... | 604/158 |
| 4,027,510 A | 6/1977 | Hiltebrandt | |
| 4,423,730 A | 1/1984 | Gabbay | |
| 4,461,305 A | 7/1984 | Cibley | |
| 4,505,414 A | 3/1985 | Filipi | |
| 4,574,806 A | 3/1986 | McCarthy | |
| 4,682,596 A | 7/1987 | Bales et al. | |
| 4,729,763 A | 3/1988 | Henrie | |
| 4,738,666 A * | 4/1988 | Fuqua .......................... | 604/514 |

(Continued)

FOREIGN PATENT DOCUMENTS

| | | |
|---|---|---|
| DE | 2 044 108 | 3/1972 |
| DE | 33 00 768 | 7/1984 |

(Continued)

OTHER PUBLICATIONS

Office Action, dated Apr. 28, 2009, Japanese Patent Application No. 2004-527715 (English-language translation provided) (JP 55-58168 cited in Japanese Office Action is a counterpart to GB 2 031 733, which was cited in Supplemental Information Disclosure Statement filed on May 9, 2005; and WO 96/23536 cited in Japanese Office Action was cited in Supplemental Information Disclosure Statement filed on May 9, 2009).

*Primary Examiner* — Victor Nguyen

(57) ABSTRACT

An orifice introducer device for introducing, e.g., a surgical device, into, e.g., an orifice of a body, includes a tubular member having a distal end and a proximal end. The distal end is adjustable between a first position for insertion into an orifice and a second position once inserted into the orifice. Alternatively, the orifice introducer device includes a distal portion having a proximal end configured to be detachably secured to the distal end of the tubular member. The distal portion is selectively detachable when the orifice introducer device is positioned in the orifice.

6 Claims, 6 Drawing Sheets

(56) References Cited

U.S. PATENT DOCUMENTS

| | | | |
|---|---|---|---|
| 4,943,277 A | 7/1990 | Bolling | |
| 5,037,379 A | 8/1991 | Clayman et al. | |
| 5,084,045 A | 1/1992 | Helenowski | |
| 5,133,360 A | 7/1992 | Spears | |
| 5,143,082 A | 9/1992 | Kindberg et al. | |
| 5,176,127 A | 1/1993 | Dormia | |
| 5,176,687 A | 1/1993 | Hasson et al. | |
| 5,183,464 A | 2/1993 | Dubrul et al. | |
| 5,186,714 A | 2/1993 | Boudreault et al. | |
| 5,190,542 A | 3/1993 | Nakao et al. | |
| 5,197,968 A | 3/1993 | Clement | |
| 5,207,684 A | 5/1993 | Nobles | |
| 5,215,521 A | 6/1993 | Cochran et al. | |
| 5,217,030 A | 6/1993 | Yoon | |
| 5,234,439 A | 8/1993 | Wilk et al. | |
| 5,304,119 A * | 4/1994 | Balaban et al. | 604/506 |
| 5,312,416 A | 5/1994 | Spaeth et al. | |
| 5,330,483 A | 7/1994 | Heaven et al. | |
| 5,336,237 A | 8/1994 | Chin et al. | |
| 5,346,497 A | 9/1994 | Simon et al. | |
| 5,354,302 A * | 10/1994 | Ko | 606/104 |
| 5,354,303 A | 10/1994 | Spaeth et al. | |
| 5,358,496 A | 10/1994 | Ortiz et al. | |
| 5,387,196 A | 2/1995 | Green et al. | |
| 5,391,156 A | 2/1995 | Hildwein et al. | |
| 5,405,378 A * | 4/1995 | Strecker | 623/1.12 |
| 5,409,487 A | 4/1995 | Jalbert et al. | |
| 5,425,357 A | 6/1995 | Moll et al. | |
| 5,437,636 A | 8/1995 | Snoke | |
| 5,447,503 A * | 9/1995 | Miller | 604/528 |
| 5,520,634 A | 5/1996 | Fox et al. | |
| 5,522,790 A | 6/1996 | Moll et al. | |
| 5,540,711 A | 7/1996 | Kieturakis | |
| RE35,352 E | 10/1996 | Peters | |
| 5,562,677 A | 10/1996 | Hildwein et al. | |
| 5,569,289 A | 10/1996 | Yoon | |
| 5,584,848 A | 12/1996 | Yoon | |
| 5,630,782 A | 5/1997 | Adair | |
| 5,653,692 A | 8/1997 | Masterson et al. | |
| 5,665,100 A | 9/1997 | Yoon | |
| 5,688,286 A | 11/1997 | Yoon | |
| 5,713,870 A | 2/1998 | Yoon | |
| 5,730,755 A * | 3/1998 | Yoon | 606/185 |
| 5,735,289 A | 4/1998 | Pfeffer et al. | |
| 5,755,769 A * | 5/1998 | Richard et al. | 623/1.2 |
| 5,765,682 A * | 6/1998 | Bley et al. | 206/363 |
| 5,807,318 A | 9/1998 | St. Goar et al. | |
| 5,807,402 A | 9/1998 | Yoon | |
| 5,817,062 A * | 10/1998 | Flom et al. | 604/174 |
| 5,830,191 A | 11/1998 | Hildwein et al. | |
| 5,863,366 A | 1/1999 | Snow | |
| 5,865,728 A | 2/1999 | Moll | |
| 5,868,711 A | 2/1999 | Kramer | |
| 5,868,779 A | 2/1999 | Ruiz | |
| 5,928,261 A | 7/1999 | Ruiz | |
| 5,931,776 A | 8/1999 | Dotolo | |
| 5,957,947 A | 9/1999 | Wattiez | |
| 6,033,420 A | 3/2000 | Hahnen | |
| 6,036,698 A * | 3/2000 | Fawzi et al. | 606/114 |
| 6,042,538 A | 3/2000 | Puskas | |
| 6,063,099 A | 5/2000 | Danks | |
| 6,146,400 A | 11/2000 | Hahnen | |
| 6,159,196 A | 12/2000 | Ruiz | |
| 6,162,235 A | 12/2000 | Vaiekunas | |
| 6,167,315 A | 12/2000 | Coe et al. | |
| 6,168,607 B1 | 1/2001 | Wattiez | |
| 6,171,282 B1 | 1/2001 | Ragsdale | |
| 6,224,608 B1 | 5/2001 | Ciccolella | |
| 6,237,605 B1 | 5/2001 | Vaska et al. | |
| 6,251,093 B1 | 6/2001 | Valley et al. | |
| 6,254,628 B1 * | 7/2001 | Wallace et al. | 623/1.12 |
| 6,261,273 B1 | 7/2001 | Ruiz | |
| 6,280,415 B1 | 8/2001 | Johnson | |
| 6,398,758 B1 * | 6/2002 | Jacobsen et al. | 604/104 |
| 6,402,722 B1 * | 6/2002 | Snow et al. | 604/164.05 |
| 6,447,444 B1 | 9/2002 | Avni et al. | |
| 6,551,350 B1 * | 4/2003 | Thornton et al. | 623/1.13 |
| 6,599,237 B1 * | 7/2003 | Singh | 600/114 |
| 6,599,304 B1 | 7/2003 | Selmon et al. | |
| 6,626,859 B2 | 9/2003 | Segesser | |
| 6,641,564 B1 * | 11/2003 | Kraus | 604/164.1 |
| 6,673,058 B2 | 1/2004 | Snow | |
| 6,899,727 B2 * | 5/2005 | Armstrong et al. | 623/1.12 |
| 7,074,232 B2 * | 7/2006 | Kanner et al. | 606/213 |
| 7,682,380 B2 * | 3/2010 | Thornton et al. | 623/1.13 |
| 2001/0001812 A1 | 5/2001 | Valley et al. | |
| 2001/0010247 A1 | 8/2001 | Snow | |
| 2001/0011170 A1 * | 8/2001 | Davison et al. | 604/500 |
| 2001/0016725 A1 | 8/2001 | Valley et al. | |
| 2001/0023334 A1 | 9/2001 | St. Goar et al. | |
| 2001/0044591 A1 | 11/2001 | Stevens et al. | |
| 2002/0013569 A1 | 1/2002 | Sterman et al. | |
| 2002/0026094 A1 | 2/2002 | Roth | |
| 2002/0026199 A1 | 2/2002 | Fortier | |
| 2002/0029783 A1 | 3/2002 | Stevens et al. | |
| 2002/0068922 A1 | 6/2002 | Peters | |
| 2002/0072741 A1 | 6/2002 | Sliwa et al. | |
| 2002/0087157 A1 | 7/2002 | Sliwa et al. | |
| 2002/0099431 A1 * | 7/2002 | Armstrong et al. | 623/1.11 |
| 2002/0104400 A1 | 8/2002 | Hillgaertner et al. | |

FOREIGN PATENT DOCUMENTS

| | | |
|---|---|---|
| DE | 44 41 333 | 5/1996 |
| EP | 0 093 101 | 11/1983 |
| EP | 0 252 214 | 1/1988 |
| EP | 653 922 | 5/1995 |
| GB | 2 022 421 | 12/1979 |
| GB | 2022421 | 12/1979 |
| GB | 2 031 733 | 4/1980 |
| GB | 2031733 | 4/1980 |
| JP | 62-233169 | 10/1987 |
| JP | 2001-137344 | 5/2001 |
| WO | WO 96/23536 | 8/1996 |
| WO | WO 01/08572 | 2/2001 |

* cited by examiner

US 8,814,785 B2

ORIFICE INTRODUCER DEVICE

CROSS-REFERENCE TO RELATED APPLICATIONS

This present application is a divisional application of U.S. application Ser. No. 10/632,271, filed on Jul. 31, 2003 now U.S. Pat. No. 7,874,981, which claims the benefit of and priority to U.S. Provisional Patent Application No. 60/400,023, filed on Jul. 31, 2002. The entire contents of each of these application is incorporated herein by reference.

FIELD OF THE INVENTION

The present invention relates to an orifice introducer device, and more particularly, to an orifice introducer device for introducing, e.g., a surgical device, into an orifice of a body.

BACKGROUND

There are many surgical procedures that require a surgical instrument to be introduced into an orifice of a body. One example of such is a surgical procedure to resect a cancerous or anomalous tissue from a gastro-intestinal tract by the introduction, e.g., insertion, of a circular stapling instrument via a patient's oral or anal cavity.

One of the problems experienced during surgical procedures of this type is that the orifice of the body may be damaged when the surgical instrument is being introduced, or has been introduced, into the orifice. This is particularly problematic when the orifice into which the surgical device is being introduced includes fragile tissue that is easily damaged when contacted, e.g., the tissues of the oral cavity. Another problem experienced during surgical procedures of this type is that the surgical instrument may be damaged when the surgical instrument is being introduced, or has been introduced, into the orifice. It may be particularly important to avoid damage to the surgical device, since a patient may also be harmed if the surgical device functions improperly.

While significant advances have been made in miniaturizing surgical instruments, there are still many surgical instruments that are almost as large as, the same size as, or larger than, the size of the orifice into which the surgical instrument is required to be introduced. Since the likelihood of damaging either the orifice or the surgical device may be increased as the size of the surgical device increases relative to the size of the orifice into which the surgical instrument is required to be introduced, conventional surgical devices and procedures still risk damage to one or both of the surgical device and the orifice.

Thus, there is a need for a device that minimizes the likelihood of damage to one or both of a surgical device and an orifice when the surgical device is introduced into the orifice.

SUMMARY

The present invention, according to various embodiments thereof, relates to an orifice introducer device for introducing, e.g., a surgical device, into, e.g., an orifice of a body. The orifice introducer device includes a tubular member having a distal end and a proximal end. The distal end is adjustable between a first position for insertion into an orifice and a second position once inserted into the orifice. Alternatively, the orifice introducer device may include a distal portion having a proximal end configured to be detachably secured to the distal end of the tubular member. The distal portion is selectively detachable when the orifice introducer device is positioned in the orifice.

In another example embodiment of the present invention, the introducer includes a tubular sheath. The diameter of the proximal end of the sheath is larger than the diameter of the distal end of the sheath. For example, the sheath may have a generally conically-shaped or tapered distal end. The diameter of the distal end may be expandable to allow passage of a surgical instrument whose diameter is larger than the diameter of the distal end. The distal end may include, for example, a slit, seam or weakened area for allowing the diameter to expand. Alternatively or additionally, the distal end may be formed of a stretchable material, such as an elastomeric material, which allows the diameter of the proximal end to expand.

In another example embodiment of the present invention, the introducer includes a sheath and a distal cap-like portion (e.g., a nose cone). The distal cap-like portion may be removably mounted to the sheath. The cap-like portion may be removed from the sheath and withdrawn or recovered through the sheath.

DETAILED DESCRIPTION

The present invention, according to various embodiments thereof, relates to an orifice introducer device that may be used, for example, for introducing or inserting, e.g., a surgical device, into an orifice, e.g., an oral cavity, of a body. For the purposes of example only, the present invention will be described hereinafter in connection with an orifice introducer device that is used for introducing or inserting a surgical device into an orifice of a body. However, it should be recognized that the present invention, in accordance with other embodiments thereof, may also be used for introducing or inserting anything, e.g., a surgeon's hand, an implantable medical device, etc., into an orifice of a body. Additionally or alternatively, it should be recognized that the present invention, in accordance with other embodiments thereof, may also be used for widening or otherwise changing the shape of an orifice of a body for purposes other than introducing or inserting something into the orifice of a body, e.g., for enabling a surgeon to view externally the interior of the orifice without introducing or inserting anything therein. Still further, it should be recognized that the present invention, in accordance with other embodiments thereof, may also be used for introducing or inserting an element into any type of orifice, not merely an orifice of a body.

Advantageously, the orifice introducer device of the present invention may function to prevent damage to either the orifice of the body or to the surgical instrument when the surgical instrument is being introduced or inserted, or has been introduced or inserted, into the orifice. Additionally or alternatively, the orifice introducer device may function so that a surgical instrument having a relatively large diameter may pass through an orifice having a relatively smaller diameter without damaging the orifice. Preferably, the orifice introducer device has a first position or arrangement in which the orifice introducer device is configured to be easily inserted into an orifice. In addition, the orifice introducer device is adjustable to a second position or arrangement in which the orifice introducer device may accommodate, e.g., a larger surgical instrument therethrough, by, for example, maintaining, stretching or otherwise changing the shape of, an orifice so that the larger surgical device may be inserted and positioned therein. Preferably, the orifice introducer device is configured to be sterilizable, enabling it to be used more than once.

Figure 1A:
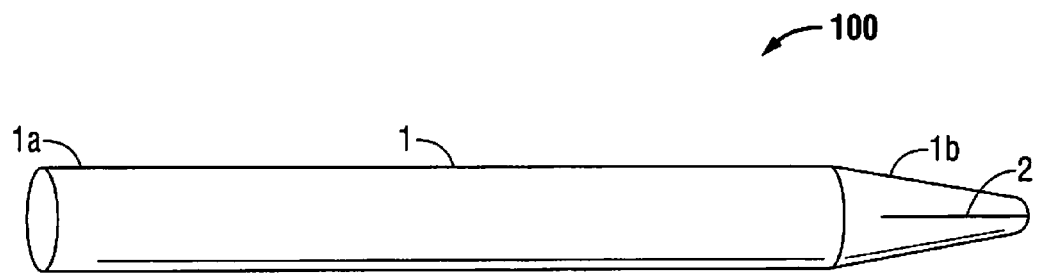
FIG. 1A is a side view that illustrates an orifice introducer device in a closed position, according to one example embodiment of the present invention.
Figure 1B:
FIG. 1B is a side view that illustrates, in an open position, the orifice introducer device illustrated in FIG. 1A.

FIGS. 1A and 1B illustrate, in a first position and a second position, respectively, an orifice introducer device 100 suitable for introducing a surgical device into an orifice of a body, in accordance with an example embodiment of the present invention. In this embodiment, the orifice introducer device 100 includes a generally tubular member 1. The tubular member 1 has a proximal end 1a and a distal end 1b. A diameter of the distal end 1b is, in the first position, smaller than the diameter of the proximal end 1a. In this embodiment, the distal end 1b is generally conical or tapered in the first position. In addition, the distal end 1b includes, in the embodiment shown, a longitudinal slit 2.

FIG. 1B illustrates the adjustability of the distal end 1b. More specifically, FIG. 1B illustrates that, in the second position, the distal end 1b is adjusted such that an diameter of the distal end 1b is increased, e.g., expanded, relative to the diameter of the distal end 1b in the first position. For instance, the inner diameter of the distal end 1b is expanded to allow a surgical device, for example a surgical device having a diameter that is larger than the diameter of the distal end 1b in the first position, to pass therethrough. In this embodiment, the distal end 1b is adjustable by the opening of the longitudinal slit 2.

In operation, the distal end 1b of the tubular member 1 is introduced into an orifice and is advanced in a distal direction until it achieves a desired position within the orifice. The relatively smaller diameter at the distal end 1b permits the orifice introducer device 100 to be more easily introduced and advanced into the orifice. Preferably, when the orifice introducer device 100 is positioned in the desired position, the proximal end 1a of the tubular member 1 remains outside of the orifice. A surgical instrument, which may be sterilizable, may then be inserted into the tubular member 1 and may be advanced distally therethrough. The surgical instrument may include, for example, a surgical instrument attached to a flexible shaft of an electromechanical driver, as described in, for example, U.S. Pat. No. 6,443,973, entitled "Electromechanical Driver Device For Use With Anastomosing, Stapling, and Resecting Instruments," filed on Jun. 2, 1999, U.S. patent application Ser. No. 09/510,927, entitled "An Electromechanical Driver And Remote Surgical Instruments Attachments Having Computer Assisted Control Capabilities, filed on Feb. 22, 2000, U.S. Pat. No. 6,517,565 entitled "Carriage Assembly for Controlling a Steering Wire Steering Mechanism Within a Flexible Shaft", filed on Feb. 22, 2000, U.S. Pat. No. 6,315,184, entitled "Stapling Device For Use With An Electromechanical Driver Device For User With Anastomosing, Stapling, And Resecting Instruments," U.S. Pat. No. 6,264,087, entitled "Parallel Jaw Device For Use With An Electromechanical Driver Device," U.S. Pat. No. 6,348,061, entitled "Vessel And Lumen Expander Attachment For Use With An Electromechanical Driver Device," U.S. Pat. No. 6,488,197, entitled "Fluid Delivery Device For Use With Anastomosing, Resecting and Stapling Instruments, filed on Feb. 22, 2000, U.S. Pat. No. 6,491,201, entitled "A Fluid Delivery Mechanism For Use With Anastomosing, Resecting And Stapling Instruments, filed on Feb. 22, 2000, U.S. Pat. No. 6,533,157, entitled "A Tissue Stapling Attachment For Use With An Electromechanical Driver Device, filed on Feb. 22, 2000, U.S. patent application Ser. No. 09/887,789, entitled "Electro-Mechanical Surgical Device," filed on Jun. 22, 2001, U.S. patent application Ser. No. 10/098,217, entitled "Trocar Device," filed on Mar. 14, 2002, U.S. patent application Ser. No. 10/128,768, entitled "Bipolar Or Ultrasonic Surgical Device, filed on Apr. 22, 2002, U.S. patent application Ser. No. 10/127,310, entitled "Imaging Device," filed on Apr. 22, 2002, U.S. Patent Application Ser. No. 60/352,726, entitled "Surgical Imaging Device," filed on Jan. 30, 2002, U.S. patent application Ser. No. 09/999,546, entitled "Surgical Device," filed on Nov. 30, 2001, U.S. patent application Ser. No. 10/094,051, entitled "A Surgical Device," filed on Mar. 8, 2002, and U.S. patent application Ser. No. 60/388,644, entitled "Surgical Device," filed on Jun. 14, 2002, each of which is expressly incorporated by reference in its entirety.

When the surgical instrument reaches the distal end 1b of the tubular member 1, the diameter of the distal end 1b may be adjusted, e.g., expanded, so as to permit at least a. portion of the surgical instrument to enter, e.g., to extend through, the distal end 1b. The expansion of the distal end 1b may be caused by, for example, the force of the surgical instrument pushing against the inner wall of the tubular member 1. In the example shown in FIGS. 1A and 1B, the distal end 1b expands via the longitudinal slit 2, e.g., by the separation of the sides 2a and 2b of the slit 2, to allow the surgical instrument to pass therethrough.

While the embodiment of FIGS. 1A to 1B illustrates that the distal end 1b of the tubular member 1 may be adjustable, e.g., expandable, alternative arrangements are possible in which the entire tubular member 1 is adjustable. Furthermore, while the embodiment of FIGS. 1A to 1B illustrates that the distal end 1b of the tubular member 1 may be adjustable, e.g., expandable, via a slit 2, alternative arrangements for providing adjustability to the distal end 1b are also possible. For example, the distal end 1b of the tubular member 1 may be formed of a stretchable material, such as an elastomeric material, whereby the force of the surgical instrument, e.g., a surgical instrument having a diameter that is larger than the diameter of the distal end 1b in a first position, against the inner wall of the tubular member 1 may stretch the material of the distal end 1b to allow the diameter of the distal end 1b to increase and the surgical instrument to pass therethrough. Alternatively or additionally, the distal end 1b of the tubular member 1 may include one or more seams, perforations, or weakened areas that tear, split or otherwise open or stretch to allow the inner diameter of the distal end 1b of the tubular member 1 to increase.

Figure 2A:
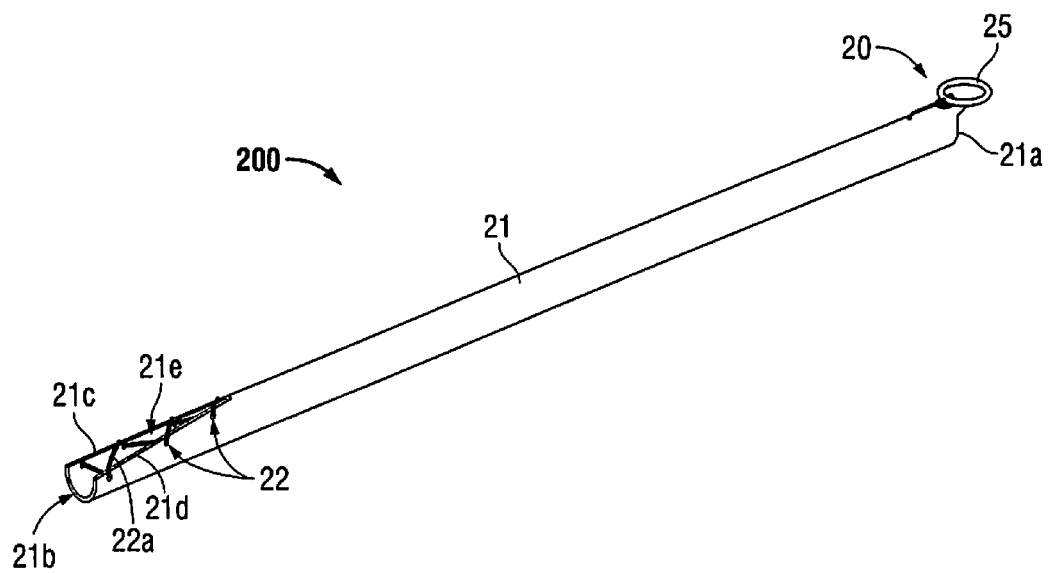
FIG. 2A is a perspective view that illustrates an orifice introducer device according to another example embodiment of the present invention.

FIGS. 2A to 2D illustrate an orifice introducer device 200 in accordance with another example embodiment of the present invention. In this embodiment, and as illustrated in FIG. 2A, the orifice introducer device 200 includes a tubular member 21 having a proximal end 21a and a distal end 21b. The distal end 21b of the tubular member 21 includes a longitudinally extending v-shaped opening or slit 21e, with a distal end of the opening 21e being wider in the open position than a proximal end of the opening 21e. In this embodiment, each of the sides 21c, 21d of the opening 21e includes a number of holes 22 through which a string 22a may be laced, threaded or corsetted. The proximal end 21a of the tubular member 21 includes an actuation device 20. The actuation device 20 may include a ring 25 or the like for gripping the string 22a.

Figure 2B:
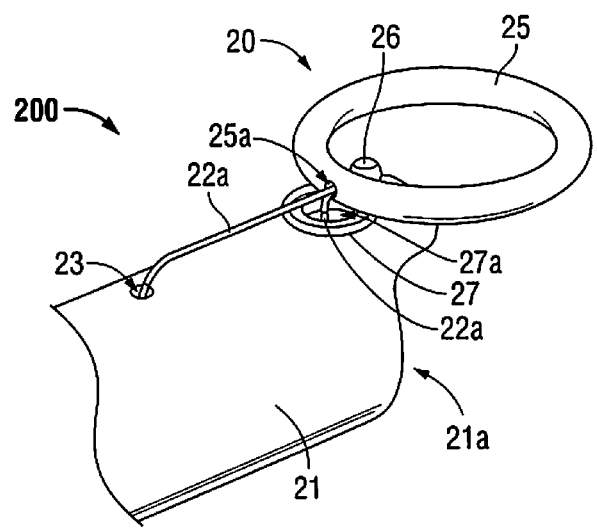
FIG. 2B is a partial perspective view that illustrates further details of a proximal end of the orifice introducer device illustrated in FIG. 2A.

As shown in further detail in FIG. 2B, the ring 25 may include a hole 25a through which both ends of the string 22a pass. Specifically, the first and second ends of the string 22a are laced within the holes 22 at the distal end 21b of the orifice introducer device 100, extend through the interior of the tubular member 21 and emerge through holes 23 and 27a, respectively. The first and second ends of the string 22a are secured to the ring 25 through the hole 25a by a crimp 26. As shown, the hole 27a may include a grommet 27 to, for example, reduce the friction of the string 22a against the sides of the hole 27a.

Figure 2C:
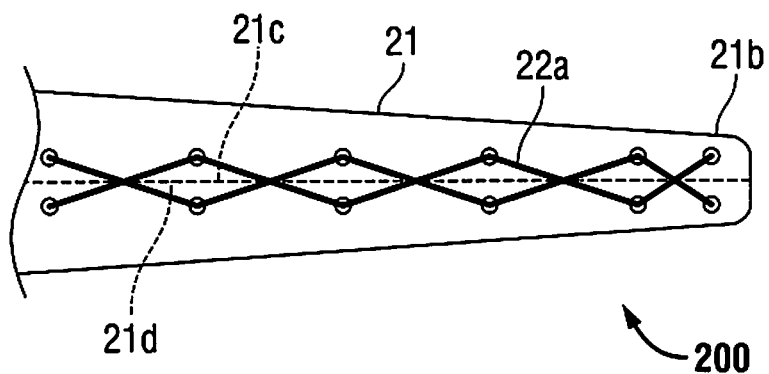
FIG. 2C is a partial side view that illustrates further details of a distal end of the orifice introducer device illustrated in FIG. 2A in a closed position.
Figure 2D:
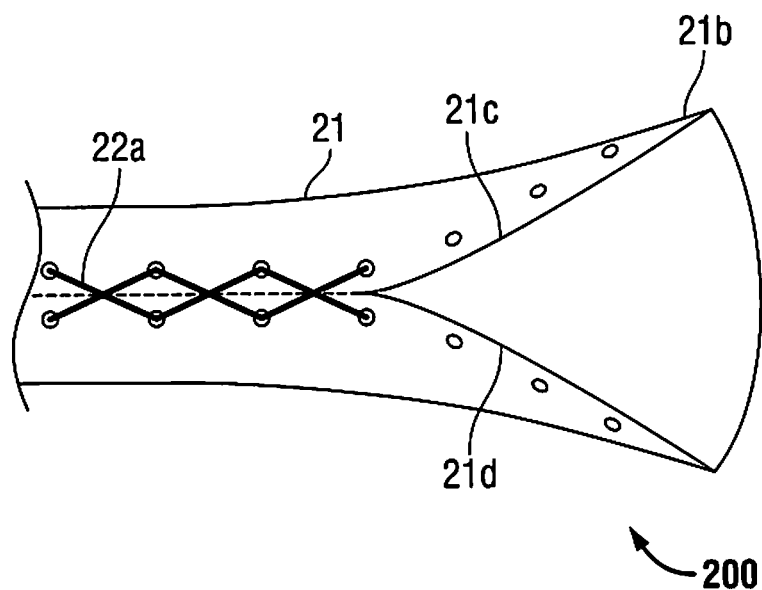
FIG. 2D is a side view that illustrates further details of the distal end of the orifice introducer device illustrated in FIG. 2A in an open position.

Prior to insertion of the orifice introducer device 200 into an orifice, the ring 25 may be moved, e.g., pulled in a proximal direction, to draw the sides 21c and 21d of the opening 21e together and thereby reduce the diameter of the distal end 21b of the tubular member 21 as illustrated in FIG. 2C. The reduced diameter of the distal end 21b of the tubular member 21 permits easier insertion of the orifice introducer device 200 into an orifice. After the orifice introducer device 200 has been inserted into an orifice and is in a desired position, the diameter of the distal end 21b of the tubular member 21 may be increased as illustrated in FIG. 2D to allow a surgical instrument to be passed therethrough. In order to increase the diameter of the distal end 21b of the tubular member 21, the ring 25 may be moved in an opposite direction, e.g., in a distal direction, thereby releasing the tension on string 22a.

It should be recognized that there are numerous different arrangements that may be employed for lacing the string 22a through the holes 22 at the distal end 21b of the tubular member 21 and for securing the string 22a to an actuation device 20, such as the ring 25, at the proximal end 21a of the tubular member 21. For instance, in another example embodiment of the present invention, the crimp 26 may be secured to the tubular member 21 at a proximal side of the hole 27a. The first and second ends of the string 22a may extend through the hole 25a of the ring 25 to be connected to the crimp 26. The ring 25 may then be moved in one direction, e.g., distally, to decrease the diameter of the distal end 21b of the tubular member 21 and in an opposite direction, e.g., proximally, to increase the diameter of the distal end 21b of the tubular member 21.

FIGS. 3A to 3G illustrate an orifice introducer device 400, and the use thereof, according to another example embodiment of the present invention. In this embodiment, a generally tubular member 300 is provided with a distal portion 310, e.g., a nose cone, at a distal end 315 thereof. The tubular member 300 may be formed from, for example, a Teflon material. The distal portion 310 is configured to be detachably mounted to the distal end 315 of the tubular member 300. The distal portion 310 may be generally conically shaped or tapered so that a distal end of distal portion 310 has a smaller diameter than a proximal end of the distal portion 310 and the tubular member 300. The distal portion 310 is generally sized and shaped to be inserted into an orifice. The distal portion 310 may have an open or closed distal end, and may be, for example, tapered, conical, frusto-conical, blunt, etc., in shape. The proximal end 325 of the distal portion 310 may be generally annularly shaped so as to be attachable to the distal end 315 of the tubular member 300. In this embodiment, the distal portion 310 may be at least partially formed from a flexible, e.g., elastomeric, material. The distal portion 310 may be, for example, stretched around the distal end 315 of the tubular member 300. Additionally or alternatively, other methods and/or devices can be used to attach the distal portion 310 to the distal end 315 of the tubular member 300, including by way of non-limiting example: an electrical connection, an adhesive, a tacky composition, a coupling member, a fastener, a material which molecularly binds with the material of the tubular member, etc.

Figure 3A:
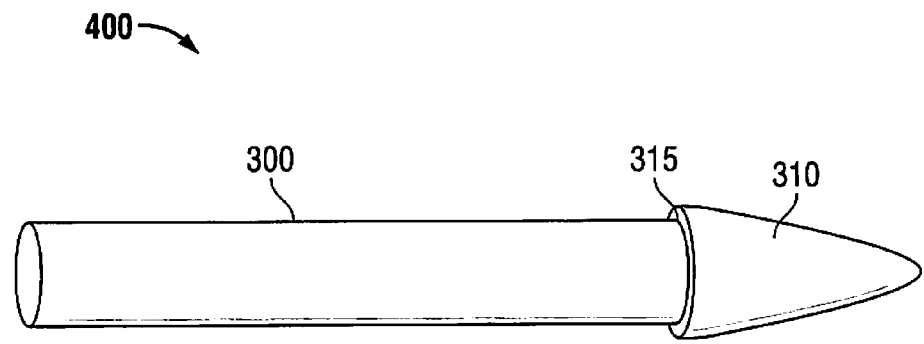
FIG. 3A is a side view that illustrates an orifice introducer device according to another example embodiment of the present invention.
Figure 3B:
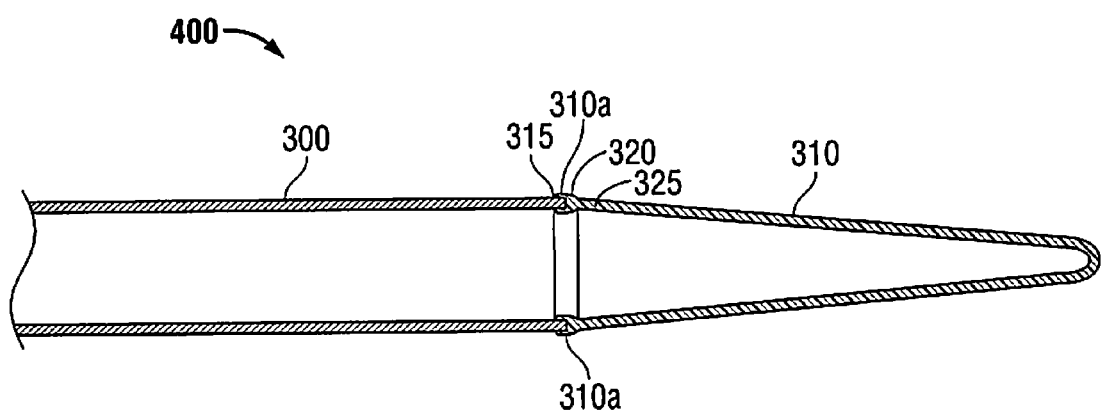
FIG. 3B is a partial, cross-sectional side view of the orifice introducer device illustrated in FIG. 3A.
Figure 3C:
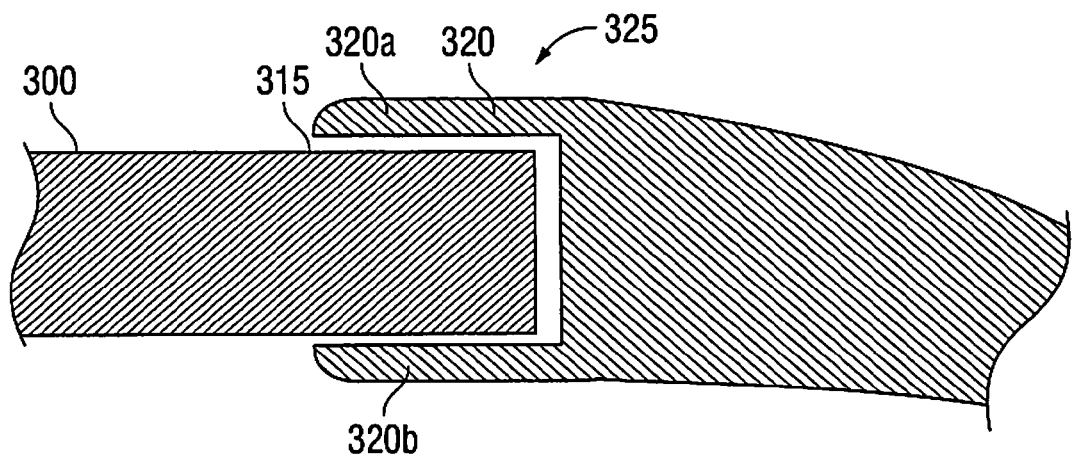
FIG. 3C is a partial, cross-sectional side view that illustrates further details of an attached distal portion of the orifice introducer device illustrated in FIG. 3A.

FIG. 3B is a partial cross-sectional view of the orifice introducer device 400 illustrated in FIG. 3A. As shown in FIG. 3B, the proximal end 325 of the distal portion 310 includes an annular groove 320. The annular groove 320 is configured to receive the distal end 315 of the tubular member 300. FIG. 3C shows further details of a portion of the annular groove 320. As shown in FIG. 3C, the annular groove 320 is configured to frictionally retain between opposing members 320a and 320b the distal end 315 of the tubular member 300.

Figure 3D:
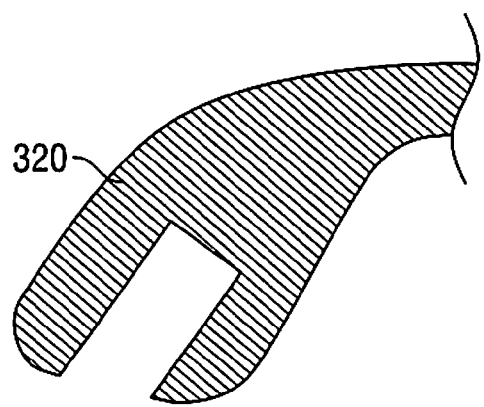
FIG. 3D is a partial, cross-sectional side view that illustrates further details of a detached distal portion of the orifice introducer device illustrated in FIG. 3A.

As noted above, in this embodiment, the distal portion 310 may be formed from a flexible, e.g., elastomeric, material. FIG. 3D illustrates the portion of the annular groove 320 shown in FIG. 3C, when the distal end 315 of the tubular member 300 is not inserted therein. As shown in FIG. 3D, the proximal end 325 of the distal portion 310 in which the annular groove 320 is housed is biased so as to bend inwardly, e.g., to have a reduced diameter, when the distal end 315 of the tubular member 300 is not inserted in the annular groove 320. Preferably, the proximal end 325 of the distal portion 310 is sufficiently biased such that, when the distal end 315 of the tubular member 300 is not inserted in the annular groove 320, the inwardly-bent proximal end 325 of the distal portion 310 has an outer diameter that is less than an inner diameter of the tubular member 300.

Figure 3E:
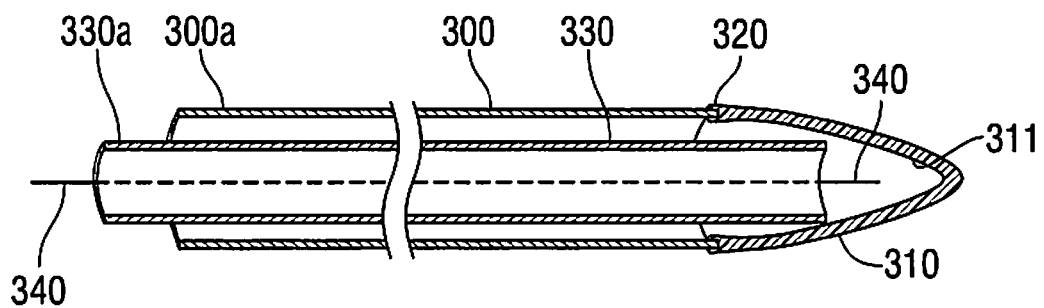
FIG. 3E is a partial, cross-sectional side view of the orifice introducer device illustrated in FIG. 3A having a second tubular body inserted therein.
Figure 3F:
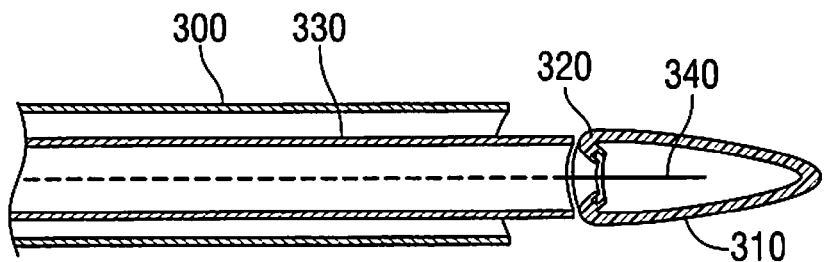
FIG. 3F is a partial, cross-sectional side view of the orifice introducer device illustrated in FIG. 3A having the second tubular body further inserted therein.
Figure 3G:
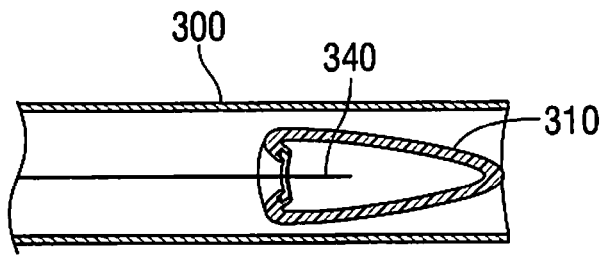
FIG. 3G is a partial, cross-sectional side view of the orifice introducer device illustrated in FIG. 3A having distal portion partially withdrawn therethrough.

FIGS. 3E to 3G illustrate the use of the orifice introducer device 300 shown in FIGS. 3A to 3D, according to one example embodiment of the present invention. In this embodiment, the orifice introducer device 400 is used with a tubular insertion device 330. For instance, FIG. 3E illustrates the orifice introducer device 400 having a tubular insertion device 330 inserted therethrough. In one embodiment, the tubular insertion device 330 is formed from a Teflon material. The tubular insertion device 330 is slidably receivable in the tubular member 300 and is configured to contact an inner wall 311 of the distal portion 310. Preferably, the tubular insertion device 330 has a sufficient length such that, when fully inserted through the tubular member 300, a proximal end 330a of the tubular insertion device 330 extends beyond a proximal end 300a of the tubular member 300 permitting manipulation of the tubular insertion device 330 by a surgeon outside the orifice.

The orifice introducer device of FIG. 3E further includes a recovery device such as a string 340 securely attached to the inner wall 311 of the distal portion 310. Preferably, a proximal end 340a of the string 340 extends beyond the proximal end of the tubular member 300 so that the string 340 can be held and/or pulled by a surgeon in a proximal direction while the tubular member 300 is left in position within the orifice.

In operation, the distal portion 310 is detachably mounted on the tubular member 300 via, e.g., the annular groove 320. The tubular member 300, including the distal portion 310 is then introduced into the orifice. Once the tubular member 300 is properly position, the tubular insertion device 330 is inserted into the tubular member 300. Alternatively, the tubular insertion device 330 may be inserted into the tubular member 300 prior to introduction and/or positioning of the tubular member 300 in the orifice. The tubular insertion device 330 is then advanced within the tubular member 300 in a distal direction, until the distal end of the tubular insertion device 330 contacts the inner wall 311 of the distal portion 310. The tubular insertion device 330 is then further distally advanced so as to cause the distal portion 310 to be detached from the proximal end 300a of the tubular member 300. Alternatively, the tubular member 300 may be pulled back proximally, while the tubular insertion device 330 is kept in place. FIG. 3F shows, for example, the distal portion 310 after it is detached from the tubular member 300.

Once the distal portion 310 is detached from the distal end 315 of the tubular member 300, the proximal end 310a of the distal portion 310 may contract. Advantageously, the proximal end 310a of the distal portion 310 contracts sufficiently such that the outer diameter of the distal portion 310 is smaller than the inside diameter of the tubular member 300. The tubular insertion device 330 then may be removed from the tubular member 300 by moving it proximally relative to the tubular member 300. Moreover, since upon contraction the outer diameter of the distal portion 310 is smaller than the inside diameter of the tubular member, the distal portion 310 may be withdrawn through the tubular member 300 by pulling the string 340 proximally. Thereafter, the tubular member 300 remains in position within the orifice, and a surgical device may be inserted into the proximal end of the tubular member 300 and advanced distally therethrough.

As seen in FIGS. 3E-3G, in use, as discussed above, the distal portion 310 is movable between a first expanded configuration when the distal portion 310 is attached to the distal end of the tubular member 300 and a second contracted configuration when the distal portion 310 is detached from the distal end of the tubular member 300. As seen in FIG. 3E, in the first expanded configuration the proximal end 310a of the distal portion 310 is oriented towards a proximal direction, and as seen in FIGS. 3F-3H, in the second contracted configuration the proximal end 310a of the distal portion 310 is oriented towards a distal direction.

Figure 3H:
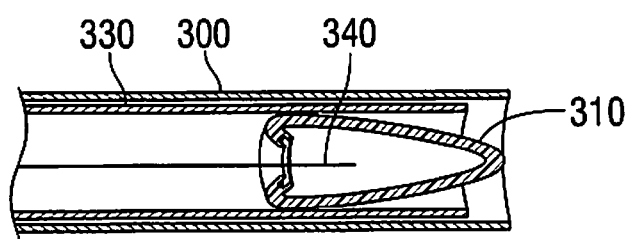
FIG. 3H is a partial, cross-section side view of the orifice introducer device illustrated in FIG. 3A having distal portion partially withdrawn through the second tubular body.

Alternatively, as seen in FIG. 3H, in one example embodiment of the present invention, the proximal end 310a of the distal portion 310 contracts sufficiently such that the outer diameter of the distal portion 310 is smaller than the inside diameter of the tubular insertion device 330, such that the distal portion 310 may be proximally withdrawn through the tubular insertion device 330 while leaving the tubular insertion device 330 in place within the tubular member 300. In this embodiment, both the tubular member 300 and the tubular insertion device 330 may remain in position within the orifice, and a surgical device may thereafter be inserted into the proximal end 330a of the tubular insertion device 330 and advanced distally therethrough.

Several embodiments of the present invention are specifically illustrated and/or described herein. However, it will be appreciated that modifications and variations of the present invention are covered by the above teachings without departing from the spirit and intended scope of the present invention.

What is claimed is:

1. An orifice introducer device, comprising:
a tubular member having a distal end and a proximal end;
the distal end being adjustable between a first position for insertion into an orifice and a second position once inserted into the orifice, wherein, in the first position, the distal end has a smaller diameter than the proximal end, and wherein the diameter of the distal end is greater in the second position relative to the first position, the distal end of the tubular member including a slit and plurality of holes extending through an outer surface of the tubular member and spaced longitudinally along its length so as to form a row of spaced-apart holes on each side of the slit in the first position; and
an actuation device having at least one aperture configured to receive therein first and second ends of a string that is positioned through the plurality of holes, the actuation device configured to control movement of the string such that proximal movement of the actuation device draws each side of the slit towards one another to move the distal end of the tubular member to the first position.

2. The orifice introducer device of claim 1, wherein at least a portion of the distal end is stretchable, and wherein the diameter of the distal end is adjusted to the second position relative to the first position by stretching the stretchable portion of the distal end.

3. The orifice introducer device of claim 1, wherein the diameter of the distal end is adjusted to the second position relative to the first position by opening of the slit.

4. The orifice introducer device of claim 1, wherein the slit defines a longitudinally extending V-shaped opening having a distal end which is wider than a proximal end.

5. The orifice introducer device of claim 1, wherein the slit defines at least a pair of sides, each of the holes being disposed in spaced relation to the sides of the slit.

6. The orifice introducer device of claim 1, wherein the string is at least one of laced., threaded, and corseted through the plurality of holes.

* * * * *